US011331260B2

(12) United States Patent
Lee et al.

(10) Patent No.: US 11,331,260 B2
(45) Date of Patent: May 17, 2022

(54) OIL-IN-WATER UV-BLOCKING COSMETIC COMPOSITION HAVING HIGH WATER RESISTANCE AND PREPARATION METHOD THEREOF

(71) Applicant: COSMAX, INC., Hwaseong (KR)

(72) Inventors: Ji Hyun Lee, Seongnam (KR); Jun Bae Lee, Yongin (KR); Sun Young Kim, Suwon (KR); Sung Yong Kim, Anyang (KR); So Youn An, Jiwang (KR); Chun Ho Park, Yongin (KR); Myeong Sam Park, Seoul (KR)

(73) Assignee: COSMAX, INC., Hwaseong (KR)

( * ) Notice: Subject to any disclaimer, the term of this patent is extended or adjusted under 35 U.S.C. 154(b) by 86 days.

(21) Appl. No.: 16/669,128

(22) Filed: Oct. 30, 2019

(65) Prior Publication Data

US 2020/0129414 A1     Apr. 30, 2020

(30) Foreign Application Priority Data

Oct. 31, 2018   (KR) .......................... 10-2018-0131781

(51) Int. Cl.
*A61K 8/90* (2006.01)
*A61K 8/06* (2006.01)
*A61Q 17/04* (2006.01)

(52) U.S. Cl.
CPC ................ *A61K 8/90* (2013.01); *A61K 8/062* (2013.01); *A61Q 17/04* (2013.01); *A61K 2800/40* (2013.01)

(58) Field of Classification Search
None
See application file for complete search history.

(56) References Cited

U.S. PATENT DOCUMENTS 6,469,132 B1   10/2002  Eisenberg et al.
2006/0134053 A1*  6/2006  L'Alloret ............... A61Q 19/00
                                                    424/70.16

FOREIGN PATENT DOCUMENTS

| CN | 1812764 A | 8/2006 |
|---|---|---|
| CN | 101255234 A | 9/2008 |
| CN | 105287241 A | 2/2016 |
| KR | 100678790 B1 | 2/2007 |
| KR | 100891260 | * 12/2008 |
| KR | 20080105249 A | 12/2008 |
| KR | 20090073368 A | 7/2009 |
| KR | 20090081954 A | 7/2009 |
| KR | 20100059351 A | 6/2010 |
| KR | 20100135537 A | 12/2010 |
| KR | 201 20006722 A | 1/2012 |
| KR | 201 40000784 A | 1/2014 |
| KR | 101 890127 B1 | 8/2018 |
| NO | 201 6159879 A1 | 10/2016 |

OTHER PUBLICATIONS

Gong et al., "Thermosensitive PEG-PCL-PEG Hydrogel Controlled Drug Delivery System: Sol-Gel-Sol Transition and In Vitro Drug Release Study", Journal of Pharmaceutical Sciences, 98, , 2009, pp. 3707-3717. (Year: 2009).*
Cho et al., "Skin Permeation and Stability of Nano-Capsulated Vitamin Emulsions Based on Biodegradable Tri-Block Copolymers", Journal of Microencapsulation, 29(8), 2012, pp. 739-746. (Year: 2012).*
KR100891260 Machine Translation from Google Patents, accessed Apr. 21, 2021 (Year: 2021).*
Piao et al., "Synthesis and characterization of PCL/PEG/PCL triblock copolymers by using calcium catalyst", Polymer, 44, (2003), pp. 2025-2031. (Year: 2003).*

* cited by examiner

*Primary Examiner* — Melissa L Fisher

(57) ABSTRACT

The present invention may provide an oil in water (O/W) cosmetic composition having water resistance and ease of facial cleansing, using an A-B-A type triblock copolymer which is included in the cosmetic, and thus may adjust the surfactant power. Further, it is possible to provide a method for imparting water resistance and ease of facial cleansing, using the A-B-A type triblock copolymer.

4 Claims, 3 Drawing Sheets

OIL-IN-WATER UV-BLOCKING COSMETIC COMPOSITION HAVING HIGH WATER RESISTANCE AND PREPARATION METHOD THEREOF

CROSS-REFERENCE TO RELATED APPLICATIONS

This application claims priority to and the benefit of Korean Patent Application No. 10-2018-0131781 filed in the Korean Intellectual Property Office on Oct. 31, 2018, the entire contents of which are incorporated herein by reference.

TECHNICAL FIELD

The present invention relates to an oil-in-water UV-blocking cosmetic composition having both high water resistance and high facial cleansing, and a preparation method thereof.

BACKGROUND ART

Due to UV-induced photoaging and an increase in incidence of skin cancer, a UV-blocking agent can be cited as a very important cosmetic technology even in terms of public health promotion. In particular, there is an increasing trend that outdoor activities such as travel, water recreation, and leisure activities are increasing, and a need for water-resistant sun products that are not removed by water and sweat.

Meanwhile, as the age of consuming UV-blocking products has been expanded to infants and babies and the frequency of use has increased, there is a need for developing a technology for a UV-blocking agent which is excellent in water resistance and easily cleaned while excellent facial cleansing has also emerged as an important quality factor that stimulates the purchase desire of consumers.

As studies on a water-resistant UV-blocking agent in the related art have focused on improving water resistance function, the water-resistant UV-blocking agent has been developed by taking a water in oil (W/O) formulation instead of an oil in water (O/W) formulation that is easily removed by water, or using a film forming agent (Korean Patent Application Laid-Open No. 10-2010-0059351).

However, when a UV-blocking agent is prepared using the aforementioned technology, there is an advantage in that water-resistant ability is excellent, but along with an issue such as heavy spreadability and stickiness, there is cumbersomeness that the face needs to be washed twice for perfect cleaning using not only cleansing oil, but also cleansing foam.

Meanwhile, a study on a UV-blocking cosmetic composition having both water resistance and facial cleansing was disclosed (Korean Patent Application Laid-Open No. 10-2010-0135537), but the water-resistant function has been implemented using a water in oil formulation, and thus, it can be said that it is a very difficult task to implement the water-resistant function using an oil in water formulation.

PRIOR ART DOCUMENT

Patent Document (Patent Document 1) Korean Patent Application Laid-Open No. 10-2010-0059351

(Patent Document 2) Korean Patent Application Laid-Open No. 10-2010-0135537

SUMMARY OF THE INVENTION

Thus, the present inventors have made intensive studies to solve the problems of the technology in the related art and develop a UV-blocking agent which is excellent in lasting and water resistance and easily cleaned, and as a result, confirmed that by the adjustment of the interfacial tension of an A-B-A type triblock copolymer which is used as a surfactant, water resistance may be improved by inhibiting re-emulsification due to water or sweat, the water resistance may be lasted for a long period of time, and the water resistance is also excellent. Further, it was also confirmed that the cosmetic composition using the surfactant could be easily cleaned by a cleaner such as soap.

In order to solve the problem, the present invention provides a triblock copolymer compound of a polyethylene glycol (PEG)-a polycaprolactone (PCL)-a polyethylene glycol (PEG), in which the triblock copolymer has a weight average molecular weight ratio of the PEG:the PCL:the PEG=1:1:1 to 1:5:1. In this case, the triblock copolymer is prepared using a PEG having a weight average molecular weight of 100 to 20,000 g/mol and a PCL having a weight average molecular weight of 1,000 to 100,000 g/mol, preferably a PEG having a weight average molecular weight of 500 to 2,000 g/mol and a PCL having a weight average molecular weight of 10,000 to 30,000 g/mol.

The present invention provides a surfactant solution composition for imparting water resistance and ease of cleaning, including a triblock copolymer compound. In this case, when the triblock copolymer compound is included in an amount of 0.001 to 1 wt % based on a total weight of the surfactant solution composition, the surfactant solution composition has an interfacial tension of 15 to 30 mN/m.

The present invention provides an oil in water UV-blocking cosmetic composition having high water resistance, including the triblock copolymer compound, in which the triblock copolymer is included in an amount of 0.1 to 10 wt %, preferably 0.5 to 5 wt %, based on a total weight of the oil in water UV-blocking cosmetic composition.

The oil in water UV-blocking cosmetic composition of the present invention further includes any one of an organic UV-blocking agent, an inorganic UV-blocking agent, and an organic and inorganic UV-blocking agent mixture in the triblock copolymer compound.

The present invention provides a method for imparting water resistance and ease of cleaning to a cosmetic composition, the method including: adding a triblock copolymer of a polyethylene glycol (PEG)-a polycaprolactone (PCL)-a polyethylene glycol (PEG), in which a weight average molecular weight ratio of the PEG:the PCL:the PEG=1:1:1 to 1:5:1. In this case, the cosmetic composition is an oil in water UV-blocking cosmetic composition.

BRIEF DESCRIPTION OF THE DRAWINGS

The accompanying drawings included as a part of the detailed description to assist understanding of the present invention provide exemplary embodiments of the present invention and explain the technical spirit of the present invention along with the detailed description.

DETAILED DESCRIPTION

Figure 1:
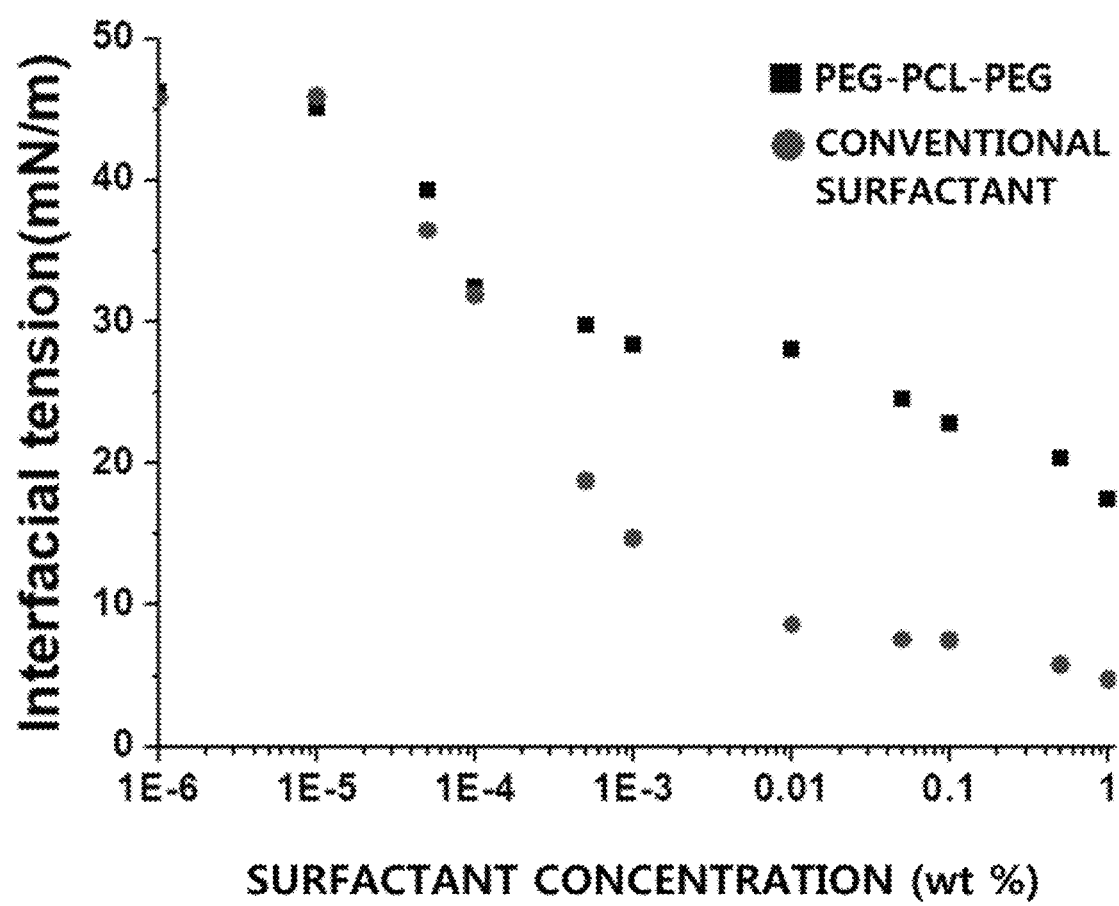
FIG. 1 is a view illustrating an interfacial tension graph of PEG-PCL-PEG and another surfactant.

An oil in water (O/W) UV-blocking agent generally contains water as a main component, and thus is preferred due to good spreadability, but has a problem in that the water resistance deteriorates and the lasting effect is low because the oil in water (O/W) UV-blocking agent may be easily removed by sweat or moisture, and when the water resistance and lasting effect are increased, the ease of cleaning deteriorates, and thus there is a problem in that the residue on the skin even after cleaning may cause skin trouble, and the like.

Therefore, the present invention provides a surfactant solution composition including a triblock copolymer compound and a UV-blocking cosmetic composition having high water resistance, including the compound, in order to negate the disadvantages.

The copolymer of the present invention is a hydrophilic-hydrophobic-hydrophilic (A-B-A) type triblock copolymer including a hydrophilic A-block and a hydrophobic B-block, and a surfactant solution composition including the same has a lower surfactant power than that of a general emulsifier, may further increase an oil phase proportion therein due to the amphiphilicity thereof, and thus may serve to improve the water resistance through the properties. Furthermore, it is possible to provide an oil in water UV-blocking cosmetic composition to which water resistance and ease of cleaning are imparted by including the copolymer.

In the present invention, the A-block of the triblock copolymer is a polymer having a formula of $(CH_2CH_2O)_n$— as a hydrophilic portion polyethylene glycol (PEG), and is water-soluble and non-ionic. The PEG has been widely used as a medical polymer due to non-toxicity and excellent biocompatibility, and is excellent in skin friendliness. For the PEG within the triblock copolymer of the present invention, the use range thereof is determined depending on the molecular weight of a polycaprolactone (PCL), and the weight average molecular weight thereof is generally 100 to 20,000 g/mol, preferably 500 to 2,000 g/mol.

In the present invention, the B-block of the triblock copolymer is a polymer with a linear structure, which has a formula of $(CH_2CH_2CH_2CH_2CH_2COO)_n$— as a hydrophobic portion polycaprolactone, and a hydrophobic polymer which has biodegradability and biocompatibility, and is not dissolved in water. Within the triblock copolymer of the present invention, a suitable molecular weight depends on the structure and molecular weight of a hydrophilic polyethylene glycol (PEG) polymer which is bonded to the polycaprolactone (PCL), and the weight average molecular weight may be generally 1,000 to 100,000 g/mol, preferably 10,000 to 30,000 g/mol, but is not limited thereto.

Therefore, the copolymer of the present invention is a hydrophilic-hydrophobic-hydrophilic (A-B-A) type triblock copolymer including the A-block of a hydrophilic polyethylene glycol (PEG) and the B-block of a hydrophobic polycaprolactone (PCL), and since the hydrophilic block PEG is located outside the triblock, and thus is easily dissolved in water, there is an advantage in that the copolymer of the present invention is easily applied and practically used considering that most of the cosmetics are in the form of an oil in water (O/W) emulsion containing water as a main component.

The triblock copolymer compound of the present invention has preferably a molecular weight ratio within a range of 1:1:1 to 1:5:1 in terms of water resistance, ease of cleaning, and formulation stability. When the PCL content is further decreased within a molecular weight ratio of 1:1:1, the possibility of re-emulsification is increased, and thus there is concern in that the compound may be washed away, and when the PCL content is increased within a molecular weight ratio of 1:5:1, the crystallization characteristics of particles are increased, and thus there is concern in that crystals may be precipitated.

The A-B block of the triblock copolymer is prepared by allowing both ends of the polycaprolactone (PCL) to react with alkyl diisocyanate (RDI) and performing the same reaction with a hydroxyl group of the polyethylene glycol (PEG), but the preparation method is not limited thereto.

During the preparation of the triblock copolymer, examples of the alkyl diisocyanate which is allowed to react with both ends include isophorone diisocyanate, tetramethylene diisocyanate, hexamethylene diisocyanate, phenylene diisocyanate, xylene diisocyanate, tolylene diisocyanate, toluene diisocyanate, cyclohexylene diisocyanate, and the like, but are not limited thereto.

Specifically, the triblock copolymer of the present invention may be synthesized via a reaction with two steps in total, in which a hydroxyl group located at both ends of a polycaprolactone (PCL) is allowed to react with alkyl diisocyanate (RDI) at 30 to 50° C. in the presence of a dibutyltin dilaurate (DBTDL) catalyst, and a hydroxyl group of the polyethylene glycol (PEG) is allowed to react with alkyl diisocyanate (RDI) at 30 to 50° C. in the presence of a dibutyltin dilaurate (DBTDL) catalyst, as indicated in the following Reaction Formula 1, but the triblock copolymer of the present invention is not limited to the synthesis method. When the temperature is less than 30° C., there is a problem in that the reaction rate is decreased, and as a result, the reaction time is prolonged, and the amount of energy consumed is increased, and when the temperature is more than 50° C., unnecessary side reaction occurs, and thus, there is a problem in that the consumption of energy required for purifying raw materials occurs. According to the following Reaction Formula 1, a triblock copolymer may be prepared at a relatively low temperature of approximately 45° C. Therefore, it is possible to lower the required energy and minimize a side reaction during the preparation.

[Reaction Formula 1]

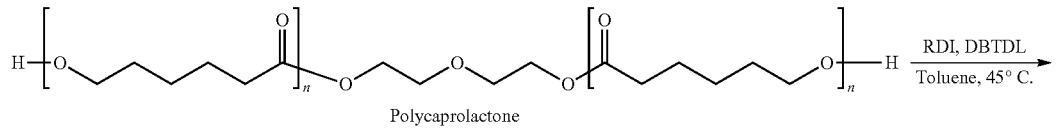

Polycaprolactone

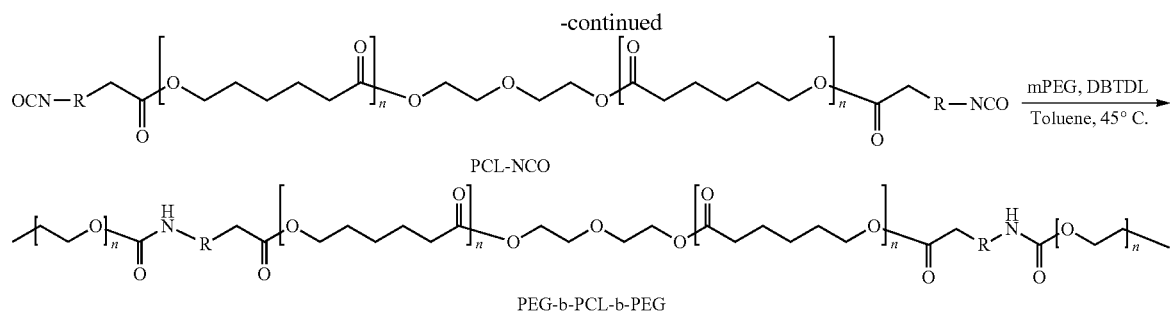

PCL-NCO

PEG-b-PCL-b-PEG

In the present invention, the A block of the triblock copolymer is a polymer having a formula of a hydrophilic portion polyethylene glycol $(CH_2CH_2O)_n$—, and the B block of the triblock copolymer is a polymer with a linear structure, which has a formula of a hydrophobic portion polycaprolactone $(CH_2CH_2CH_2CH_2CH_2COO)_n$—. In the present invention, a triblock copolymer prepared by setting the weight average molecular weight ratio of the PEG-PCL-PEG at 1:1 to 5:1 was used, and the triblock copolymer may be prepared with various molecular weight ratios according to the molecular weight of the polycaprolactone used.

2. Preparation of Oil in Water UV-blocking Agent

In order to compare the oil in water UV-blocking cosmetic composition including the triblock copolymer (Example 1) with the present Example 1, the cosmetic composition in Comparative Examples 1 and 2 was prepared with the composition (unit: wt %) as shown in the following Table 1. Example 1 and Comparative Example 1 are an oil in water (O/W) formulation, and Comparative Example 2 is a general water in water (W/O) cream-type formulation.

In Example 1 and Comparative Examples 1 and 2, each raw material was weighed in a beaker according to each component and content described in the following Table 1, and then uniformly mixed and emulsified for 5 minutes using a homogenizer at a temperature of 75 to 80° C. When the emulsification is completed, each cosmetic composition was prepared by cooling the resulting emulsified mixture to room temperature in a water bath, and removing bubbles.

TABLE 1

| Component | Content (wt%) Comparative Example 1 | Comparative Example 2 | Example 1 |
| --- | --- | --- | --- |
| Butylene glycol | 5.0 | 5.0 | 5.0 |
| Disodium EDTA | 0.02 | 0.02 | 0.02 |
| Xanthan gum | 0.05 | 0.05 | 0.05 |
| Silica | 1.5 | 1.5 | 1.5 |
| Ceteareth-20 | 0.1-10 | — | — |
| PEG-PCL-PEG Triblock copolymer | — | 2.0 | 2.0 |
| PEG-10 Dimethicone | — | 3.0 | — |
| Ethanol | 13.0 | — | 13.0 |
| Ester oil | 7.0 | — | 7.0 |
| Silicone oil (Cyclopentasiloxane) | — | 15.0 | — |
| Magnesium sulfate | — | 0.8 | — |
| Organic UV-blocking agent component | 17.2 | 15.0 | 17.2 |
| Inorganic UV-blocking agent component | 4.0 | 8.5 | 4.0 |
| Glycerin | 5.0 | 5.0 | 5.0 |
| Preservative | Appropriate amount | Appropriate amount | Appropriate amount |
| Thickener | 0.5-1.5 | 0.5-1.5 | 0.5-1.5 |
| Purified water | to 100 | to 100 | to 100 |

As the ester oil, ethylhexyl palmitate and/or neopentyl glycol diheptanoate were/was used.

The thickener of the present invention may be an acrylates/$C_{10-30}$ alkyl acrylate crosspolymer, and the preservative may be phenoxyethanol and/or glyceryl caprylate.

EXPERIMENTAL EXAMPLE 1

Evaluation of Interfacial Tension of Surfactant

The surfactant power of each of the surfactants used during the preparation of Example 1 and Comparative Examples 1 and 2 was evaluated, and the detailed evaluation methods and results are as follows.

In the present Experimental Example 1, the interfacial tension of each of the surfactants contained in Comparative Examples 1 and-2 and Example 1 was measured by a Du Nouy ring method using a Sigma 700/701 force tensiometer (Biolin Scientific, Sweden). For the measurement of the interfacial tension, aqueous solutions in which each surfactant was dissolved were prepared at a concentration of 0.000001 wt %, 0.00001 wt %, 0.0001 wt %, 0.001 wt %, 0.01 wt %, 0.1 wt %, and 1 wt %, and the results of measuring the interfacial tension of the PEG-PCL-PEG aqueous solution and an conventional surfactant dodecane are illustrated in FIG. 1.

As illustrated in FIG. 1, it could be confirmed that the interfacial tension value of the PEG-PCL-PEG showed a higher interfacial tension value than the conventional surfactant. That is, the value means that the PEG-PCL-PEG triblock copolymer shows a lower surfactant ability than the conventional surfactant, and the surfactant ability (physical property) could be expected to prevent the re-emulsification when the PEG-PCL-PEG triblock copolymer contacts water.

EXPERIMENTAL EXAMPLE 2

Macroscopic Evaluation of Water Resistance of UV-Blocking Cosmetic Composition

Figure 2:
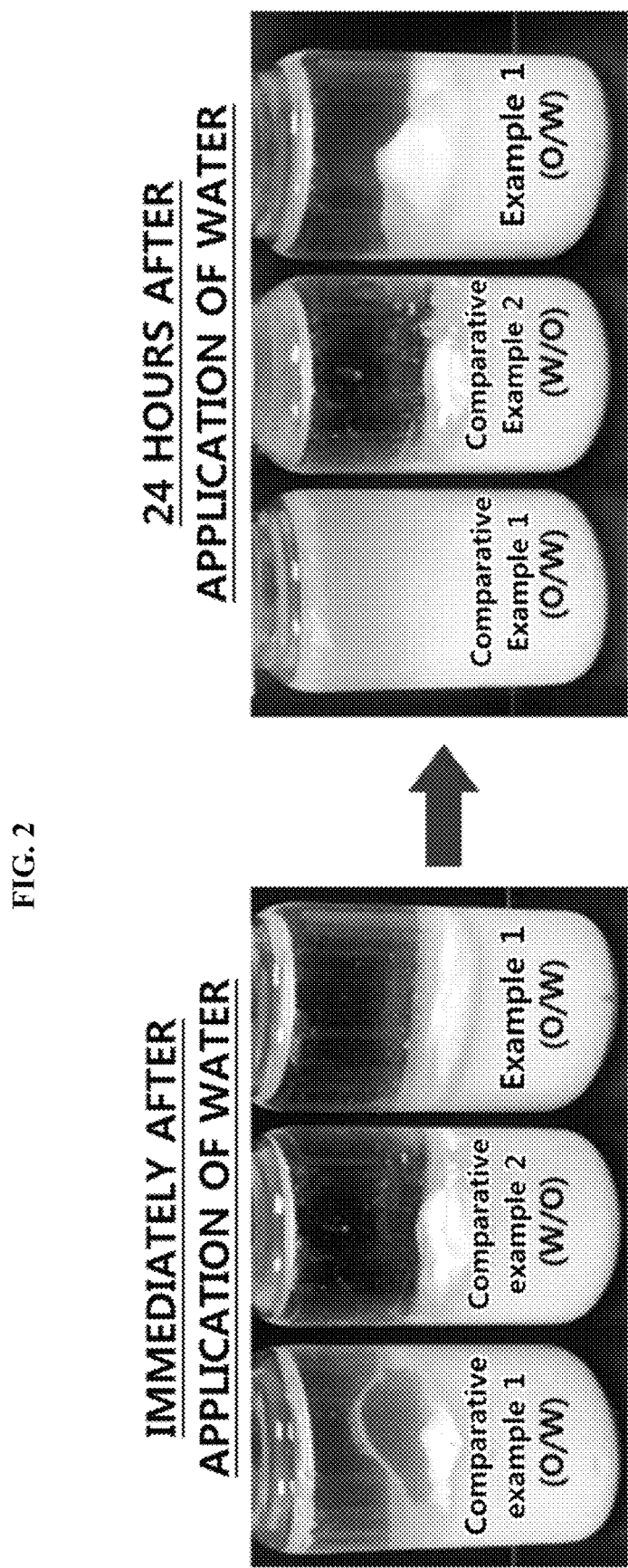
FIG. 2 is a photograph illustrating the re-emulsification of each cosmetic composition by water.

Confirmation of Water Resistance Effect by Inhibiting Re-Emulsification by Water In order to see the water resistance effects of the UV-blocking cosmetic compositions in Comparative Examples 1 and 2 and Example 1, the degree to which the re-emulsification occurred when water was introduced was evaluated by the unaided eye. For the test method, after 10 g of a UV-blocking cosmetic composition was put into a vial, 20 mL of water was flowed thereon so as not to be mixed with the composition, and then the re-emulsification was evaluated by the unaided eye from the degree to which the cosmetic composition and water were mixed over time, and the results are illustrated in FIG. 2.

As a result of comparing the degrees of re-emulsification by the unaided eye, it was confirmed that Example 1 was better than Comparative Example 1, and the effects were shown to be similar to Comparative Example 2 as a W/O formulation. This is because Comparative Example 1 of the O/W type prepared using the conventional surfactant becomes turbid due to the occurrence of re-emulsification as the Comparative Example contacts water, or the outer phase in Comparative Example 2 is an oil, and thus is not miscible with water, and the change in formulation rarely occurs over time. Meanwhile, even though Example 1 of the O/W type prepared using the PEG-PCL-PEG surfactant is an O/W formulation, Example 1 showed excellent water resistance which is similar to that of Comparative Example 2 which is a W/O formulation.

EXPERIMENTAL EXAMPLE 3

Evaluation of Water Resistance and Ease of Cleaning Through Cleaning of UV-Blocking Cosmetic Composition In order to visualize the evaluation of water resistance effects and ease of cleaning of Comparative Examples 1 and 2 and Example 1, a macroscopic evaluation was performed using a UV camera VISIA-CR (Canfield Scientific, USA) to capture Comparative Examples 1 and 2 and Example 1 on the UV-NF mode, and the detailed evaluation methods and results are as follows.

By the test method, a test site with a size of 2 cm * 2 cm was set on the antebrachial flexure 5 cm from the wrist of a subject. Each UV-blocking cosmetic composition was uniformly applied at a density of 2 mg/cm$^2$ onto a clean test site of the subject, and then naturally dried for 20 minutes, and the case where the composition was washed 50 times by rolling 50 mL of lukewarm water under the same pressure or the case where the composition was cleaned using a foam cleanser was captured by a UV camera VISIA-CR (Canfield Scientific, USA). In this case, the water resistance effect was determined by the degree to which each UV-blocking cosmetic composition remained after cleaning with lukewarm water, and the degree of the ease of facial cleansing (washability) of a formulation was determined by the image of each residual cosmetic composition after cleaning using lukewarm water and a foam cleanser.

Figure 3:
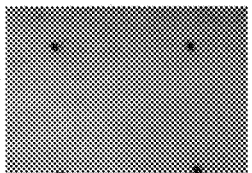
FIG. 3 is a view illustrating a result confirming water resistance and ease of cleaning with a macroscopic evaluation photograph using lukewarm water and foam cleanser in the formulations.

As a result, as illustrated in FIG. 3, it was confirmed that both Comparative Examples 1 and 2 and Example 1 exhibited the same light and shade before being washed with water (after being applied). After cleaning with rolling of lukewarm water, a large amount of UV-blocking agent fell off from Comparative Example 1 of the O/W formulation prepared by using the conventional surfactant, and thus the light and shade was thinly exhibited, and in Comparative Example 2 of the W/O formulation and Example 1 prepared using the PEG-PCL-PEG surfactant, the light and shade was more thickly exhibited, and the PEG-PCL-PEG surfactant was only slightly brighter than after being applied, and exhibited a similar light and shade. In photographs taken by the UV camera, it can be determined that the thicker the light and shade appears, the less the UV-blocking raw material is washed off by water, and thus, Example 1 has better water resistance. Through this, it could be qualitatively confirmed that Example 1 including the PEG-PCL-PEG surfactant had water-resistant effects. The results of confirming water resistance through the rate of change in brightness are shown in Table 2. As can be confirmed in Table 2, it was confirmed that when the composition is cleaned with only lukewarm water, the rate of change was shown to be 56.4%, and thus Example 1 had remarkably excellent water resistance as compared to Comparative Example 1.

After Comparative Examples 1 and 2 and Example 1 were cleaned with a foam cleanser, the ease of cleaning was determined through filming with the UV camera. All of the three compositions showed the same light and shade before being washed with water (after being applied), but after cleaning with a foam cleanser, a large amount of the UV-blocking agent in Comparative Example 2 of the W/O formulation only remained, and both Comparative Example 1 and Example 1 including the PEG-PCL-PEG surfactant showed an easy cleaning power against a foam cleanser. The results of confirming ease of cleaning through the rate of change in brightness are shown in Table 2. As can be confirmed in Table 2, it was confirmed that when the composition is cleaned with a foam cleanser, the rate of change was shown to be 14.23%, and thus Example 1 had remarkably excellent ease of cleaning as compared to Comparative Example 2.

TABLE 2

| Product Name | Before application | After application | Washing with lukewarm water + rolling 50 times | Washing with lukewarm water + rolling 50 times + foam cleanser |
|---|---|---|---|---|
| Comparative Example 2 | 0.0 | 100.0 | 57.50 | 20.63 |
| Comparative Example 1 | 0.0 | 100.0 | 16.47 | 13.92 |
| Example 1 | 0.0 | 100.0 | 56.4 | 14.23 |

EXPERIMENTAL EXAMPLE 4

Evaluation of in Iivo Water Resistance of UV-Blocking Cosmetic Composition

In order to see the water resistance effects of the UV-blocking cosmetic composition in Example 1 of the O/W formulation prepared using the PEG-PCL-PEG on the human body skin, the water resistance UV-blocking index was evaluated by an external clinical agency DERMAPRO Ltd. The test method measures and determines the minimum amount of erythema of a non-application site, and measures and determines the minimum amount of erythema of a sample application site, after a subject suitable for the test was selected. After the sample was applied, the minimum amount of erythema and SPF of the sample were determined by irradiation with UV light based on the minimum amount of erythema of the non-application site after four times of water immersion (80 minutes) and drying. In this case, it is determined that when the water resistance unreliable interval of the subject is 50% or more, Example 1 has water resistance.

TABLE 3

| Product Name | Average water resistance ratio (%) | Water resistance unreliable interval |
|---|---|---|
| Example 1 | 56.3 ± 4.5 | 54.3 |

Since the water resistance unreliable interval for 10 subjects was 50% or more (54.3%), it was confirmed that the cosmetic composition of the present invention had very water resistance.

According to the present invention, a PEG-PCL-PEG triblock copolymer may be prepared by containing a surfactant in a predetermined amount to lower the surfactant power and inhibit the re-emulsification by water, thereby implementing water resistance as an oil in water formulation. Further, it was confirmed that the water resistance is also excellent by confirming that the water resistance is lasted for a long period of time.

The present invention provides a highly water-resistant UV-blocking cosmetic composition which has water resistance, is excellent in facial cleansing, and thus is easily cleaned by only soap or cleansing foam.

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

Representative exemplary embodiments of the present invention have been described in detail, but it is to be understood by a person with ordinary skill in the art to which the present invention pertains that the above-described exemplary embodiments may be variously modified without departing from the scope of the present invention. Therefore, the right scope of the present invention should not be defined as being limited to the described exemplary embodiments, and should be defined by not only the claims to be described below, but also those equivalent to the claims.

What is claimed is:

1. An oil in water UV-blocking cosmetic composition having high water resistance, comprising the triblock copolymer compound of a polyethylene glycol (PEG)-a polycaprolactone (PCL)-a polyethylene glycol (PEG) in an amount of 0.5 to 5 wt % based on a total weight of the cosmetic composition,
    wherein the triblock copolymer compound has a weight average molecular weight ratio of the PEG:the PCL:the PEG=1:1:1 to 1:5:1,
    wherein the PEG in the triblock has a weight average molecular weight of 500 to 2,000 g/mol, and
    wherein when the triblock copolymer compound is comprised in an amount of 0.001 to 1 wt % based on a total weight of solution composition, the solution composition has an interfacial tension of 15 to 30 mN/m.

2. The oil in water UV-blocking cosmetic composition of claim 1, wherein the oil in water UV-blocking cosmetic composition further comprises any one of an organic UV-blocking agent, an inorganic UV-blocking agent, and an organic and inorganic UV-blocking agent mixture.

3. An oil in water UV-blocking cosmetic composition having high water resistance, comprising the triblock copolymer compound of a polyethylene glycol (PEG)-a polycaprolactone (PCL)-a polyethylene glycol (PEG) in an amount of 0.5 to 5 wt % based on a total weight of the cosmetic composition,
    wherein the triblock copolymer compound has a weight average molecular weight ratio of the PEG:the PCL:the PEG=1:1:1 to 1:5:1, and
    wherein the PCL in the triblock has a weight average molecular weight of 10,000 to 100,000 g/mol.

4. An oil in water UV-blocking cosmetic composition having high water resistance, comprising the triblock copolymer compound of a polyethylene glycol (PEG)-a polycaprolactone (PCL)-a polyethylene glycol (PEG) in an amount of 0.5 to 5 wt % based on a total weight of the cosmetic composition,
    wherein the PEG of each PEG block has a weight average molecular weight of 500 to 2,000 g/mol and the PCL has a weight average molecular weight of 10,000 to 30,000 g/mol.

* * * * *